United States Patent
Blackbourn et al.

(10) Patent No.: US 6,426,430 B1
(45) Date of Patent: Jul. 30, 2002

(54) METHOD FOR REDUCTION OF POTASSIUM IN AN INTEGRATED PROCESS FOR THE PRODUCTION OF 2,6—NDA

(75) Inventors: Robert Lawrence Blackbourn, Houston, TX (US); Raymond Lawrence June, Singapore (SG)

(73) Assignee: Mossi & Ghisolfi Oversears, S.A. (LU)

( * ) Notice: Subject to any disclaimer, the term of this patent is extended or adjusted under 35 U.S.C. 154(b) by 0 days.

(21) Appl. No.: 09/643,355

(22) Filed: Aug. 22, 2000

Related U.S. Application Data

(60) Provisional application No. 60/151,607, filed on Aug. 30, 1999, provisional application No. 60/151,498, filed on Aug. 30, 1999, provisional application No. 60/151,603, filed on Aug. 30, 1999, provisional application No. 60/151,529, filed on Aug. 30, 1999, provisional application No. 60/151,489, filed on Aug. 30, 1999, provisional application No. 60/151,604, filed on Aug. 30, 1999, provisional application No. 60/151,606, filed on Aug. 30, 1999, provisional application No. 60/151,589, filed on Aug. 30, 1999, provisional application No. 60/151,497, filed on Aug. 30, 1999, provisional application No. 60/151,590, filed on Aug. 30, 1999, provisional application No. 60/151,578, filed on Aug. 30, 1999, and provisional application No. 60/151,602.

(51) Int. Cl.$^7$ .............................................. C07C 51/347
(52) U.S. Cl. ........................ 562/481; 562/482; 562/486
(58) Field of Search .................................. 562/481, 482, 562/486

(56) References Cited

U.S. PATENT DOCUMENTS

| | | | |
|---|---|---|---|
| 3,671,578 A | * | 6/1972 | Ogata et al. |
| 4,212,991 A | * | 7/1980 | Choulet et al. |
| 5,859,294 A | * | 1/1999 | Hashimoto et al. |

* cited by examiner

*Primary Examiner*—Paul J. Killos
*Assistant Examiner*—Héctor M Reyes
(74) *Attorney, Agent, or Firm*—Renner, Kenner, Greive, Bobak, Taylor & Weber

(57) ABSTRACT

Disclosed is a method for reducing alkali metals in aromatic dicarboxylic acids produced by disproportionation or rearrangement of an alkali salt of a mono- or dicarboxylic acid to levels acceptable for polymerization which comprises:

a) Washing the aromatic dicarboxylic acid with water in a ratio of about 5:1 water to acid at a temperature of about 70–200° C.;

b) Introducing the washed aromatic dicarboxylic acid into a reactor characterized by minimal backmixing, such as a pipe reactor, and reacting the washed aromatic dicarboxylic acid in the pipe reactor at about 100–200° C.;

c) Directing the aromatic dicarboxylic acid exiting the pipe reactor to a centrifuge to separate the solid aromatic dicarboxylic acid from water containing contaminants;

d) Optionally, combining the solid aromatic dicarboxylic acid again with water in a ratio of about 5:1 at a temperature of about 100–200° C. to further reduce levels of alkali metals.

6 Claims, No Drawings

METHOD FOR REDUCTION OF POTASSIUM IN AN INTEGRATED PROCESS FOR THE PRODUCTION OF 2,6— NDA

CROSS REFERENCE

This application is related to U.S. application Ser. Nos. 60/151,602, 60/151,607, 60/151,498, 60/151,603, 60/151,529, 60/151,489, 60/151,604, 60/151,606, 60/151,589, 60/151,497, 60/151,590, and 60/151,578, filed of even date Aug. 30, 1999.

FIELD OF THE INVENTION

This invention is generally related to the purification of aromatic dicarboxylic acids, especially 2,6-naphthalene dicarboxylic acid. More particularly, this invention is related to a practical method of reducing potassium in the final product to acceptable levels for subsequent polymerization.

BACKGROUND OF THE INVENTION

Polymer grade aromatic dicarboxylic acids are important as starting materials for a number of polyester fibers, polyester films, resins for bottles and containers, and the like. Naphthalene dicarboxylic acids, especially 2,6-naphthalene dicarboxylic acid (hereafter referred to as 2,6-NDA) are starting materials for polyethylene naphthalates, which can also be employed in the manufacture of fibers, films, and resins. Presently in the art, it is very difficult to produce polymer grade 2,6-NDA and only dimethyl 2,6-naphthalene dicarboxylate, the methyl ester of the more desirable 2,6-NDA is commercially available for use in making polymers such as polyethylene naphthalate.

When aromatic dicarboxylic acids are produced by a disproportionation reaction, such as described in U.S. Pat. No. 2,823,231 and U.S. Pat. No. 2,849,482, for example, where an alkali metal salt of a mono- or dicarboxylic acid is disproportionated to produce isomers of the salt of the desired dicarboxylic acids, the product often retains undesirable amounts of the alkali metal, most often potassium.

The goal of a number of processes for purification of aromatic dicarboxylic acids, and 2, 6-naphthalene dicarboxylic acid in particular, is to reduce these alkali metals along with other impurities to the lowest levels possible, but there is still a need in the art for methods of reducing impurities and alkali metals to levels acceptable for use in polymers.

Methods of purification of aromatic dicarboxylic acids, especially 2,6-naphthalene dicarboxylic acid are known in the art. Where 2,6-NDA is produced by disproportionation, common methods for purification include filtration, acidification and crystallization. See, for example, U.S. Pat. Nos. 2,849,482; 3,631,096; 3,671,578; and 3,952,052. It is possible to remove significant amounts of color bodies and impurities, but it is still difficult to obtain polymer grade 2,6-NDA.

Currently in the art the most common process for making 2,6 NDA starts with relatively expensive o-xylene and butadiene feedstocks, as discussed, for example, in U.S. Pat. No. 5,510,563 and U.S. Pat. No. 5,329,058 and incurs substantial yield losses of these starting materials. Following the synthesis and purification of 2,6 dimethylnaphthalene (2,6 DMN), 2,6 DMN is oxidized to produce crude NDA product which forms as a solid with impurities trapped within. Therefore, in such processes, esterification to naphthalene dicarboxylate (NDC) is necessary to eliminate the impurities, as discussed in U.S. Pat. Nos. 5,254,719 and 4,886,901. Direct purification of the crude NDA via hydrogenation has been suggested by U.S. Pat. No. 5,292,934, but requires a difficult and expensive high temperature hydrogenation in the presence of a solvent. Another proposed purification scheme requires the use of nitrogen containing species. (See U.S. Pat. No. 5,770,764 and U.S. Pat. No. 5,859,294). Crystal size and morphology is important in either case, whereas the novel process disclosed herein can optionally avoid the issue of controlling particle size of the final product.

Currently NDC is commercially available, but NDA is not, presumably because of the difficulty of producing polymerization grade NDA without esterifying to NDC. Ideally, if NDA were available commercially at a competitive price, NDA would be preferred over NDC as the starting monomer for PEN. Alternative routes to NDA based on the rearrangement reaction have been plagued with difficulties associated with handling solids, the inefficient recycling of potassium, and ineffective integration from feedstock through final product. Although various improvements have been suggested over the years, there is still a distinct need in the art for an economical, integrated process for producing polymer grade 2,6-NDA, the preferred monomer for the production of polyethylenenaphthalate (PEN). Copending U.S. application Ser. No. 60/151,577 (Attorney's Docket #TH1432) discloses a novel integrated process for producing the preferred 2,6-naphthalene dicarboxylic acid.

It would represent a distinct advance in the art if a method were available to reduce the levels of alkali metals, particularly potassium in product 2,6-NDA to levels which are acceptable for polymerization to polyethylene naphthalate.

SUMMARY

In accordance with the foregoing, the present invention provides a method for reducing alkali metals in aromatic dicarboxylic acids produced by disproportionation or rearrangement of an alkali salt of a monocarboxylic acid to levels acceptable for polymerization which comprises:

a) Washing the aromatic dicarboxylic acid with water in a ratio of about 5:1, water to acid, at a temperature of about 70–200° C., b) Introducing the washed aromatic dicarboxylic acid into a reactor characterized by minimal backmixing, such as a pipe reactor, and reacting the washed aromatic dicarboxylic acid in said reactor in approximately a 5:1 water to acid ratio at about 100–200° C.;

c) Directing the aromatic dicarboxylic acid exiting the pipe reactor to a centrifuge to separate the solid aromatic dicarboxylic acid from water containing contaminants;

d) Optionally, combining the solid aromatic dicarboxylic acid again with water in a ratio of about 5:1 at a temperature of about 100–200° C. to further reduce levels of alkali metals.

In the preferred embodiment, the invention makes it possible to reduce the level of potassium in product 2,6-naphthalene dicarboxylic acid to less than 50 ppm.

DETAILED DESCRIPTION

In the preferred embodiment the aromatic dicarboxylic acid which is treated in the present invention is 2,6-NDA produced by a process which incorporates disproportionation of an alkali metal salt of a mono- or dicarboxylic acid.

Following disproportionation the crude product is in the form of an isomer of a dialkali salt of 2,6 -NDA. Salts formed by the reaction can be transformed into the corresponding acids by acidifying the solution with acids or by introducing carbon dioxide into the solution and then separating the free acids from the acidified solution. The salt mixture produced by the reaction may also be transformed directly into derivatives of the acids, such as, for example, their esters or halides, and these derivatives can be purified, if desired, by fractional distillation.

The product treated in the present invention can be produced by the process described in copending Ser. No. 60/151,577 (Attorney's Docket #1432), incorporated by reference herein in its entirety. In that process, after disproportionation the solid product consisting of K2NDA isomers is washed and the liquid is filtered to remove catalyst and coke particles.

The liquid carrying mixed organic salts is introduced into a two-stage evaporative crystallization section where the K2NDA is selectively precipitated, $KHCO_3$ is recycled, and the purified K2NDA is redissolved with additional $H_2O$. Then the purified K2NDA is passed through an activated carbon bed.

Next, the dipotassium salt of 2,6-NDA, (K2NDA) is selectively precipitated using $CO_2$ to make the KHNDA solids which are then disproportionated into 2,6 -NDA and K2NDA. The product of disproportionation is centrifuged to yield a 2,6 NDA slurry, and a centrate containing predominantly 2,6 K2NDA and $KHCO_3$. The product 2,6-NDA contains from about 60–1000 ppm potassium on a dry basis. It is desirable to reduce the amount of potassium to 50 ppm or less.

The key to obtaining polymer grade product with <50 ppm potassium without using excessive water is the combined use of a 5:1 water wash and a pipeline reactor to drive the reaction to completion and/or remove trace $K^+$.

The 2,6-NDA and trace KHNDA are directed into a water wash. In the water wash a ratio of about 3 to 8 parts water is added to one part 2,6-NDA solid and KHNDA and reacted at a temperature of about 90 to 180° C., for up to about one hour. Good results were observed washing with about 5 parts water and heating to about 150° C. for about 30 minutes. The higher temperature is preferred because it affords higher solids loading.

The 2,6-NDA and KHNDA are then introduced into a reactor of the type known as a pipeline reactor, characterized by plug flow kinetics. In a plug flow reactor very little, if any, backmixing of product with feed occurs, as contrasted with a stirred vessel reactor or pipe loop reactor. Reactors of the type known in the art as turbulent flow would also be effective.

The temperature in the pipeline reactor should be in the range of 100–200° C. The preferred range is about 140–170° C., with a temperature in the range of 150° C. providing good results.

The residence time in the pipeline reactor can vary. The slurry is reacted at plug flow conditions to drive the KHNDA disproportionation reaction toward completion and to remove trace potassium. In example 1 it was found that the desired results were achieved under plug flow conditions in about 30 minutes to an hour.

The contents of the pipeline reactor is directed to a centrifuge where trace contaminants are removed and recycled back to the KHNDA disproportionation reactor.

A second water wash is optional, but is included in the preferred embodiment. This second wash makes it possible to reduce the ppms of potassium to less than 50 ppm. The 2,6-NDA is combined with water, again at a ratio of about 3–8 parts water to one part 2,6-NDA and a temperature of about 100° to 200° C. Good results were achieved using about a five fold excess water, and increasing the temperature to about 1500C. Example 2 demonstrates the reduction of potassium levels to <50 ppm.

The slurry containing the product 2,6-NDA is directed to a last centrifuge to separate the product from the water.

The 2,6 -NDA solid can be dried by conventional means, apparent to those skilled in the art, or as described, for example, in U.S. Pat. No. 5,292,934 or U.S. Pat. No. 5,840,968, incorporated by reference herein. However, where dry handling of the solid product is practiced, particle size control can be critical and the handling of 2,6- NDA particles is difficult and costly.

As mentioned above, it has previously not been possible in the art to obtain commercially available 2,6-NDA which is acceptable for polymerization. With the present invention it is now possible to produce 2,6-NDA with less than 50 ppm potassium. Other impurities are not as much of a problem as in the prior art either using the novel integrated process of copending Ser. No. 60/151,577 (Docket #TH1432) which avoids the isolation of purified naphthoic acid using a novel hydrodebromination step.

The process of copending Ser. No. 60/151,577 (Docket #1432) makes it possible to spring impurities. Therefore, it is now possible to produce 2,6-NDA with a low level of impurities and less than 50 ppm potassium. 2,6 -NDA of this quality can also be transported in a water slurry which is convenient for close coupling with a process for making polyethylene naphthalate (PEN), thus avoiding the difficulties associated with product particle size control, drying, and solids handling. This is discussed in more detail in U.S. Ser. No. 60/151,603(Attorney's Docket #1598).

The present invention will be more clearly understood from the following examples. It is understood that these examples are presented only to illustrate certain embodiments of the invention and are not intended to limit the scope thereof.

EXAMPLE 1

Example 1 describes the method used to reduce the ppms of potassium in the 2,6 NDA solid product. In Example 1 first KHNDA was disproportionated and the resulting 2,6 NDA solid product was washed with water in a ratio of 5:1, water to solids, at temperatures of 95° C. and 135° C. for periods of time as indicated. The levels of potassium were checked and then the solids were reslurried twice to obtain the ppmw of potassium recorded in the last column. This example employs kinetics which are expected in the pipe line reactor with turbulent flow, or a batch reactor, or plug flow reactor. Results are recorded in Table 1:

TABLE 1

| | Temp. °C | Res. Time | KHNDA (% W) | After Washing K+ (ppmw) *, ** | Reslurry #1 (5/1 water to solid) | | | Reslurry #2 (5/1 water to solid) | | |
|---|---|---|---|---|---|---|---|---|---|---|
| | | | | | Temp °C | Res. Time | K+ (ppmw) ** | Temp °C | Res. Time | K+ (ppmw) |
| 1-1 | 135 | 1.0 hr | 7.5 | 73–140 | 1-1a | 95 | 0.5 hr 80–150 | 1-1b | 95 | 0.5 hr 54–109 |
| 1-2 | 135 | 2.0 hr | 7.5 | 71–140 | 1-2a | 95 | 0.5 hr 57–106 | 1-2b | 95 | 0.5 hr ?–105 |
| 1-3 | 135 | 1.0 hr | 5 | 21–74 | 1-3a | 95 | 0.5 hr 15–36 | 1-3b | 95 | 0.5 hr 9–45 |
| 1-4 | 95 | 1.0 hr | 5 | 1300*** | 1-4a | 95 | 0.5 hr 8–42 | | | |
| 1-5 | 95 | 1.0 hr | 5 | 520 | 1-5a | 95 | 0.5 hr 49**** | | | |
| 1-6 | 95 | 0.5 hr | 5 | 3800 | 1-6a | 95 | 0.5 hr 46 by ICP | | | |
| 1-7 | 95 | 1.0 hr | 5 | 400 | 1-7a | 25 Ambient | 0.5 hr 79 by ICP | | | |

\* K + after approximately a 5:1 water rinse of the filter cake at reaction temperature.
\*\* Also real K+ number is closer to the higher number in the bracket; confirmed by ICP on prior runs (Plasma Jet)
\*\*\*Filter not kept at reaction temperature
\*\*\*\*XRF without BCK subtraction = high on the numbers

EXAMPLE 2

Example 2 demonstrates the preferred conditions for purifying the solid 2,6 NDA with increased solids loading. The residence time was about 30 minutes to an hour, the temperature was about 150° C., and the disproportionation reaction was assisted by the use of about 150 psig $CO_2$. The solids were then washed with water in an approximately 5:1 ratio of water to NDA and left at 150° C. for 0.5 hours. The solids were then reslurried once. Results are recorded in Table 2.

TABLE 2

| | $CO_2$ Assisted 150 psig system | Temp °C | Res. Time | Feed KHNDA (% W) | K+ (ppmw) In NDA After Disproportionation & 5:1 water wash | Temp (°C.) | Res. Time | K+ (ppmw) Without background Subtraction |
|---|---|---|---|---|---|---|---|---|
| 24049-199-1 | Yes | 150 | 0.5 hr | 8 | 69 | 150 | 0.5 hr | <40 |
| 24049-199-2 | Yes | 150 | 0.5 hr | 9 | 630 | | | |
| 24049-199-3 | Yes | 150 | 1.0 hr | 9 | 280 | | | |
| 24049-199-4 | Yes | 150 | 1.0 hr | 9 | 290 | | | |
| 24049-199-5 | Yes | 150 | 1.0 hr | 10 | 330 | 150 | 0.5 hr | <33 |
| 24049-199-8 | No | 150 | 1.0 hr | 8 | 320 | 150 | 0.5 hr | <45 |
| 24049-199-10 | No | 150 | 1.0 hr | 9 | 290 | | | |

We claim:

1. A method for reducing alkali metals in aromatic dicarboxylic acids produced by disproportionation or rearrangement of an alkali salt of a monocarboxylic acid which comprises:
   a) Washing the aromatic dicarboxylic acid with water in a ratio (grams:grams) of about 4–8:1 water to acid at a temperature of about 70–200° C.,
   b) Introducing the aromatic dicarboxylic acid in water into a reactor characterized by minimal backmixing and reacting the aromatic dicarboxylic acid in water in said reactor at a temperature of about 100–200° C.;
   c) Directing the aromatic dicarboxylic acid in water exiting said reactor to a centrifuge to separate the solid aromatic dicarboxylic acid from water containing contaminants;
   d) Optionally, combining the solid aromatic dicarboxylic acid again with water in a ratio (grams:grams) of about 5:1 at a temperature of about 100–200° C. to further reduce levels of alkali metals.

2. The process of claim 1 wherein the aromatic dicarboxylic acid is 2,6-naphthalene dicarboxylic acid and the alkali metal is potassium.

3. The process of claim 2 wherein the reactor is selected from a pipeline reactor and a plug flow type reactor.

4. The process of claim 3 further comprising washing the 2,6-naphthalene dicarboxylic acid with water in a ratio of about 5 parts water to one part 2,6-NDA at a temperature of about 140–160°; reacting the 2,6 -NDA in a pipeline reactor for up to about one hour at about 140–170° C.; and centrifuging the contents exiting the pipeline reactor to separate the 2,6 -NDA from water containing contaminants.

5. The process of claim 4 which further comprises washing the 2,6-NDA a second time, after reacting in the pipe reactor, with water at a ratio of about five parts water to one part 2,6-NDA at a temperature of about 130–170° C. for up to about one hour.

6. The process of claim 5 wherein the amount of potassium in the product 2,6-naphthalene dicarboxylic acid is reduced to less than 50 ppmw.

* * * * *